US010247717B2

(12) United States Patent
Fang

(10) Patent No.: US 10,247,717 B2
(45) Date of Patent: Apr. 2, 2019

(54) METHOD OF EFFICIENT ACQUISITION OF SOIL DATA USING IMAGE MAPPING

(71) Applicant: SAFENET INTERNATIONAL LLC, Arlington Heights, IL (US)

(72) Inventor: Joseph Y. Fang, South Barrington, IL (US)

(73) Assignee: SAFENET INTERNATIONAL LLC, Arlington Heights, IL (US)

( * ) Notice: Subject to any disclaimer, the term of this patent is extended or adjusted under 35 U.S.C. 154(b) by 37 days.

(21) Appl. No.: 15/679,677

(22) Filed: Aug. 17, 2017

(65) Prior Publication Data

US 2019/0017984 A1  Jan. 17, 2019

Related U.S. Application Data

(60) Provisional application No. 62/532,731, filed on Jul. 14, 2017.

(51) Int. Cl.
| | |
|---|---|
| *H04N 7/18* | (2006.01) |
| *G01N 33/24* | (2006.01) |
| *G01J 3/28* | (2006.01) |
| *G01N 27/04* | (2006.01) |
| *G01N 21/3563* | (2014.01) |

(Continued)

(52) U.S. Cl.
CPC ........... *G01N 33/24* (2013.01); *B64C 39/024* (2013.01); *G01J 3/2823* (2013.01); *G01N 21/3563* (2013.01); *G01N 27/04* (2013.01); *G06K 9/0063* (2013.01); *G06K 9/209* (2013.01); *G06K 9/2018* (2013.01); *B64C 2201/123* (2013.01); *G01J 2003/2826* (2013.01); *G01N 2033/245* (2013.01); *G01N 2201/127* (2013.01)

(58) Field of Classification Search
CPC .... G01N 33/24; G01N 21/3563; G01N 27/04; G01N 2033/245; G01N 2201/127; G01J 3/2823; G01J 2003/2826; G06K 9/0063; G06K 9/209; G06K 9/2018; B64C 39/024; B64C 2201/123
USPC ......................................................... 348/144
See application file for complete search history.

(56) References Cited

U.S. PATENT DOCUMENTS 7,536,025 B2 * 5/2009 Folchetti ................ G06Q 30/00
  382/100
9,401,030 B2 * 7/2016 Nelan .................... G06T 7/0002
(Continued)

FOREIGN PATENT DOCUMENTS

WO WO-2017004074 A1 * 1/2017 ............... A01G 7/00

OTHER PUBLICATIONS

Gao et al, Study on the effects of returning farmland to forest project on the eco-environment vulnerability of mudanjiang (Year: 2010).*

*Primary Examiner* — Shan E Elahi
(74) *Attorney, Agent, or Firm* — Bishop, Diehl and Lee, Ltd.

(57) ABSTRACT

A system and method for determining soil properties, such as organic matter (OM), pH, and electrical conductivity (EC) using a mobile soil sample station and a multispectral sensor mounted on a multi-rotors or professional fixed-wing drone. Combined with an optional fixed soil sampling station and mathematical modeling (built with Cloud-based database with iterative learning process) calibration, the system and method improve soil analysis by enabling real time examination, as well as improving affordability and efficiency.

18 Claims, 10 Drawing Sheets

(51) Int. Cl.
*G06K 9/20* (2006.01)
*G06K 9/00* (2006.01)
*B64C 39/02* (2006.01)

(56) References Cited

U.S. PATENT DOCUMENTS

| | | | |
|---|---|---|---|
| 9,733,355 B2* | 8/2017 | Chan | G01S 13/89 |
| 2012/0010788 A1* | 1/2012 | Dearborn | A01B 79/005 |
| | | | 701/50 |
| 2012/0201415 A1* | 8/2012 | Bredehoft | G06K 9/00657 |
| | | | 382/100 |
| 2015/0106434 A1* | 4/2015 | Fiene | H04L 67/42 |
| | | | 709/203 |
| 2016/0063420 A1* | 3/2016 | Tomii | G06Q 10/06315 |
| | | | 705/7.24 |
| 2016/0253595 A1* | 9/2016 | Mathur | G06Q 50/02 |
| | | | 706/12 |
| 2017/0042081 A1* | 2/2017 | Zumbach | G01N 1/08 |
| 2017/0090068 A1* | 3/2017 | Xiang | G01W 1/10 |

* cited by examiner

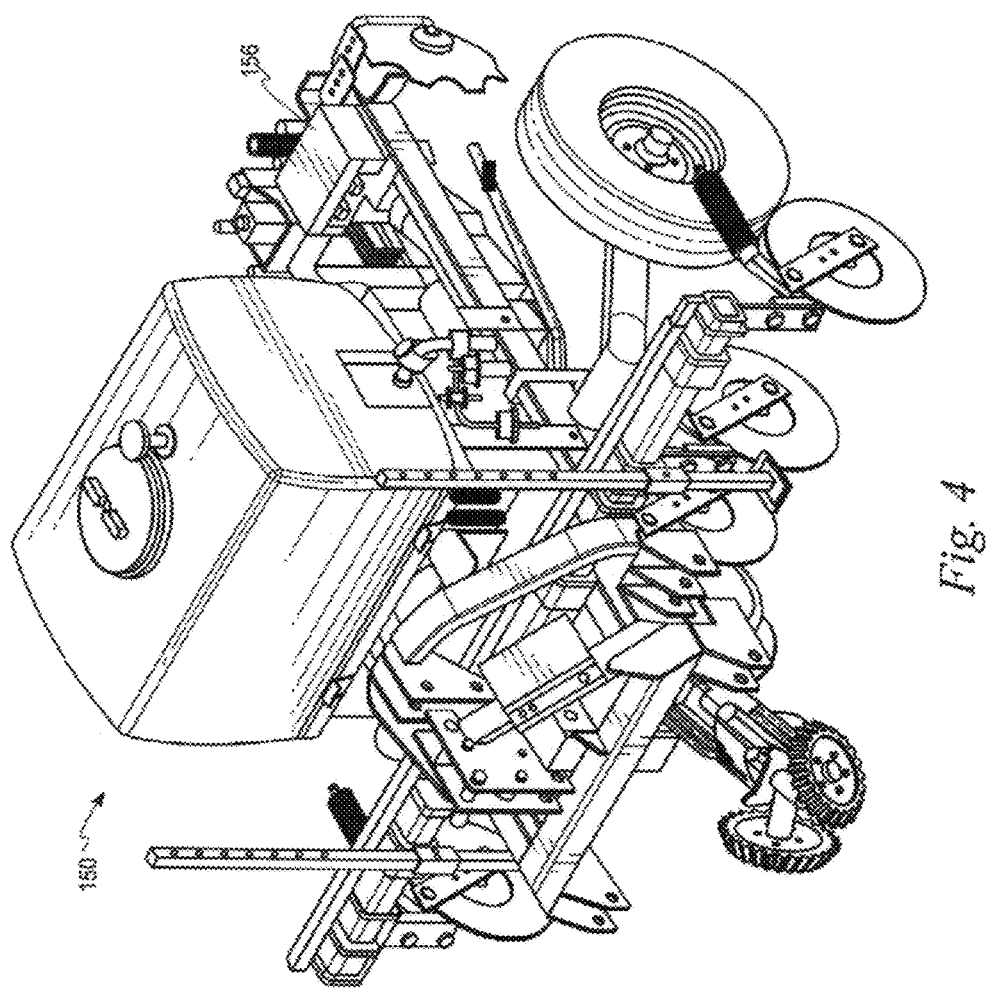

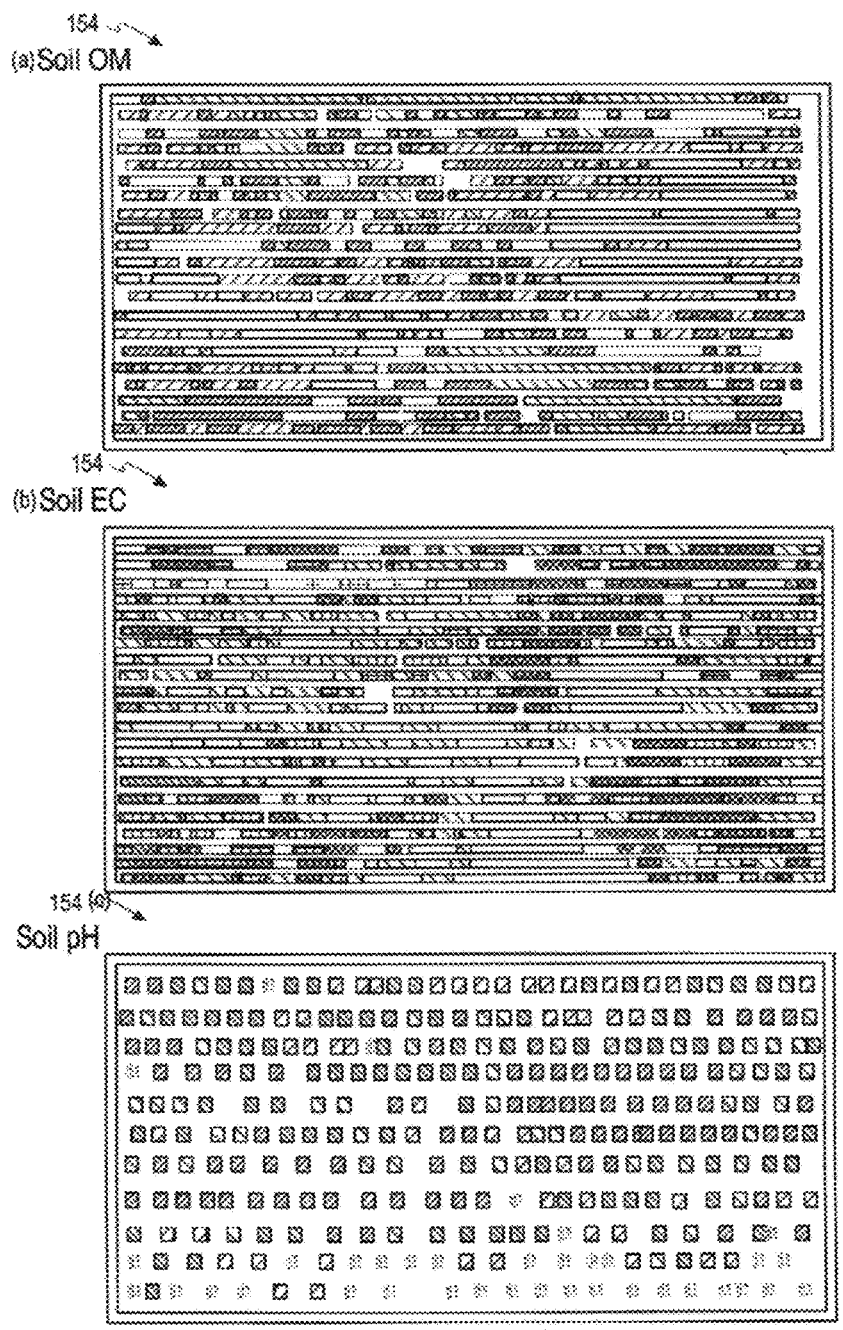
Fig. 9

METHOD OF EFFICIENT ACQUISITION OF SOIL DATA USING IMAGE MAPPING

RELATED APPLICATION

The present application claims the filing benefit of related U.S. Provisional Application No. 62/532,731, titled "METHOD OF EFFICIENT ACQUISITION OF SOIL DATA USING IMAGE MAPPING" and having a filing date of Jul. 14, 2017. The '731 Provisional Application is hereby incorporated by reference.

TECHNICAL FIELD OF THE INVENTION

The present application relates to data collection and image mapping. Particularly, the application relates to collection of soil data, such as organic matter (OM), electric conductivity (EC) and pH, as well as methods, devices and systems for efficiently collecting and mapping such data.

BACKGROUND OF THE INVENTION

Soil is a complex, living, changing and dynamic component of an agroecosystem. It is subject to alteration, and can be either degraded or wisely managed. A thorough understanding of the ecology of the soil ecosystem is a key part of designing and managing agroecosystems in which the long-term fertility and productive capacity of the soil is maintained, or even improved. Such an understanding begins with knowledge of how soil is formed in a given ecological region, and includes integration of all the components that contribute to the structure and function of the entire soil ecosystem. A great many biological, chemical and physical factors determine soil quality. By measuring some of these components and determining how they respond to management in an agricultural context, a foundation for assessing the health of the soil can be established. Ultimately, indicators of sustainability can be grounded in the assessment of soil conditions and how they change as a result of the choices a farmer makes in managing the agroecosystem. Three components of particular interest to farmers are soil pH, organic content (OC) and electrical conductivity.

Soil acidity or pH is a measure of the hydrogen ion (H+) activity in the soil solution, in this case water, and is specifically defined as the −log 10 of the hydrogen ion concentration. Soil pH will rise or fall depending on the impact of a range of factors, including farming practices. If as a result of these impacts the soil pH falls below or rises above certain optimum levels for biological and chemical activity, the soil will become much less productive Organic matter plays many important roles in the soil ecosystem, all of which are of importance to sustainable agriculture. The organic content (OC) is one of the best indicators of soil quality, especially when the soil can be observed over a period of time. Measuring soil organic matter content with high precision and accuracy requires sophisticated equipment and involved techniques.

Finally, soil electrical conductivity (EC) is a measurement that correlates with soil properties that affect crop productivity, including soil texture, cation exchange capacity (CEC), drainage conditions, organic matter level, salinity, and subsoil characteristics.

The collection of soil property data related to these three components can be very costly and time consuming, and despite the criticality of the information, many fields go untested due to these cost and time commitments. This is a known and growing problem in agroecosystem management.

There are believed to be only four methods currently in use or under development to exam soil properties. Each of these four (4) systems uses a Cloud-based database to both accumulate examined data at varying situations and to build models for mapping calibration. The four known soil examination methods are:

1. Manual acquisition of soil samples from a field, and examining in a soil lab to obtain OM, EC, and pH data. These results can be uploaded to a Cloud-based database with an associate to the sampling position (GPS), administration location or a corresponding field number.
2. Automatic acquisition of soil samples from a field using a plurality of stationary base stations, each equipped with a mobile transmitter. Soil data is acquired through station soil sensors and transmitted from a station to a Cloud-based database. The data includes the known location and identification of each reporting station.
3. Veris Technologies (Salina, Kans.) manufactures and sells vehicle-mounted Soil Sensor Systems such as the MSP™ and MSP3™ with on-going soil sampling (for example, see http://www.veristech.com/the-sensors/msp). The sensor system is moved through a field (for example, via a farm tractor), while OM, EC, and pH sensor modules on the MSP™ allow a user to obtain data in an "on-the-go" fashion. The on-board software allows a user to determine how to acquire OM, EC, and pH on the field as the field is mapped to a preset grid of separate OM, EC, and pH grids respectfully (see FIG. 9). Data can be uploaded to a Cloud-based database for further calibration and analysis.
4. SoilOptix Technologies (http://www.practicalprecision.ca/solutions/soiloptix/) currently markets a passive sensor system mounted to the front of an ATV. The sensor system measures four nuclides that are naturally present in soil, including uranium, potassium-40, thorium and cesium. Data is collected, and variations in radiation levels are used to construct soil survey maps which are determine where the soil samples take place. With the soil sample confirmation, a group of soil texture maps are constructed which represent the standard N-P-K, OM, pH, etc.

The first and second soil acquisition procedures take soil samples at a fix location. Manually taking samples requires experience to determine where to take soil samples (and possible average multiple samples to one) to send to a soil laboratory to examine a days' process. Conversely, automatically taking soil sample has ability to transit soil data to a Cloud-based database in minutes. However, mobility may have a much higher maintenance cost for sensors and other equipment and can be a slow, inefficient method for data collection, especially in large fields. While both procedures are in practice, neither is useful in solving all of the problems associated with field soil sampling and mapping.

MSP™ (see system No. 3 above) is a product made by the Veris Technologies. The device is moved through the field, and with a limited number of soil samples needed to calibrate, it can produce fairly accurate OM, EC, and pH measurement. The system of the present application uses this product to acquire soil properties in fields as determined by an aerial survey.

The SoilOptix™ (system No. 4 above) design has a passive sensor to collect gamma ray release through the top 12 inches of soil. However, due to very low energy emitting from the soil, it requires a fairly large amount of soil samples to build accurate database. With a sensor system mounted on an ATV, the process can be extremely slow and the coverage area may be further limited by the terrain of the land.

These and other problems are addressed by the present device and methods to provide a system and methods with numerous advantages in operation and effectiveness over prior art. The present invention uses an unmanned aerial vehicle (UAV) with a penetrating multispectral sensor to scan fields from the air. The system also uses MSP to acquire data and map the field by moving a sensor system through the field. A calibration is performed using soil sample results from predetermined locations based on the spectral image (survey). Finally, a mathematic module is used to calculate a correlation between the spectral image information and the grid of MSP soil properties, including OM, EC, and soil pH.

SUMMARY OF THE INVENTION

The following disclosure is directed to improved systems and methods for mapping soil properties for a field, such as a farm field.

Generally speaking, the system for mapping soil properties of a field comprises a multispectral image mapping system, a mobile soil sensor system, a database for collecting and storing soil data from the mobile system and for collecting images produced by the mapping system, and a computing system electronically coupled to the database and configured to use the soil data.

More specifically, the multispectral image mapping system is configured to produce a multispectral image for a first land area having a defined periphery, the multispectral image having a plurality of discernible regions. The mobile soil sensor system moves over a second land area and includes a soil sampling mechanism which takes periodic samples of soil as the system moves, a GPS module for determining a location for each soil sample, at least a first soil sensor for determining a desired property of each soil sample, and memory for recording soil sample properties and location as soil data. The preferred computing system uses the soil data from the mobile system to produce at least one grid representing a second land area with soil property values.

In an embodiment, the computing system comprises a correlation system for aligning the at least one grid onto a corresponding portion of the multispectral image and correlating soil data to discernible regions of the corresponding portion to create mapped regions, and an interpolation system for assigning soil properties to remaining portions of the first land area which are not part of the second land area, wherein the assigned soil properties are based on the mapped regions.

In an embodiment, the system comprises an unmanned aerial vehicle (UAV) for flying above an area to be mapped, wherein the spectral image mapping system is mounted to the unmanned aerial vehicle (UAV). Preferably, the UAV comprises a drone.

In alternate embodiments, the system comprises at least one fixed soil sampling station positioned at a known location within the first land area and configured to take and test periodic samples of soil proximate the fixed station position. Further, a soil lab may be used for analyzing manually sampled soil as a means of verifying the accuracy of the mobile system when a change in properties occurs. These are calibration events.

In embodiments, the system comprises a plurality of fixed soil sampling stations wherein at least one fixed soil sampling station is positioned in the field corresponding to each discernible region of the multispectral image. The fixed soil sampling station uses real time acquisition ability (e.g., minutes) to calibrate any variance between the multispectral image mapping system and the mobile soil sensor system, as these events occur at different times.

Regarding the method of mapping soil properties of a field, the method comprises the steps of obtaining a multispectral image of an entire field, such as a farm field, acquiring soil property data for a plurality of soil samples by moving a mobile soil sensor system over a predetermined portion of the entire field, wherein the predetermined portion is smaller than the entire field, constructing a grid of the soil property data, correlating the grid and its soil property data to a corresponding area of the multispectral image, and using the correlated grid and soil property data to extrapolate a soil property to a remainder of the field, the remainder of the field being a portion not covered by the predetermined area, based on the multispectral image of the remainder of the field.

In an embodiment of the method, the step of obtaining a multispectral image comprises the steps of flying an unmanned aerial vehicle equipped with a multispectral imaging camera over the entire field, taking a plurality of pictures of the field, and constructing the multispectral image from the plurality of pictures.

In a further embodiment, the method comprises the steps of positioning a fixed soil sampling station in an area on the field, testing soil samples from the fixed station to determine actual soil properties which is then used to calibrate the initial soil property data of the plurality of soil samples with the multispectral image.

These and other aspects of the present invention will be more readily understood from a reading of the following detailed description in conjunction with the appended drawing figures.

BRIEF DESCRIPTION OF THE DRAWINGS

For the purpose of facilitating an understanding of the subject matter sought to be protected, there are illustrated in the accompanying drawings embodiments thereof, from an inspection of which, when considered in connection with the following description, the subject matter sought to be protected, its construction and operation, and many of its advantages should be readily understood and appreciated.

FIG. 4 illustrates an embodiment of vehicle-mounted soil sensors (MSP) moving through a field to create a soil sample grid using GPS;

FIG. 9 is an illustration of three soil sample data grids indicating (a) OM, (b) EC, and (c) pH of the soil; and;

DETAILED DESCRIPTION OF PREFERRED EMBODIMENTS

Figure 1:
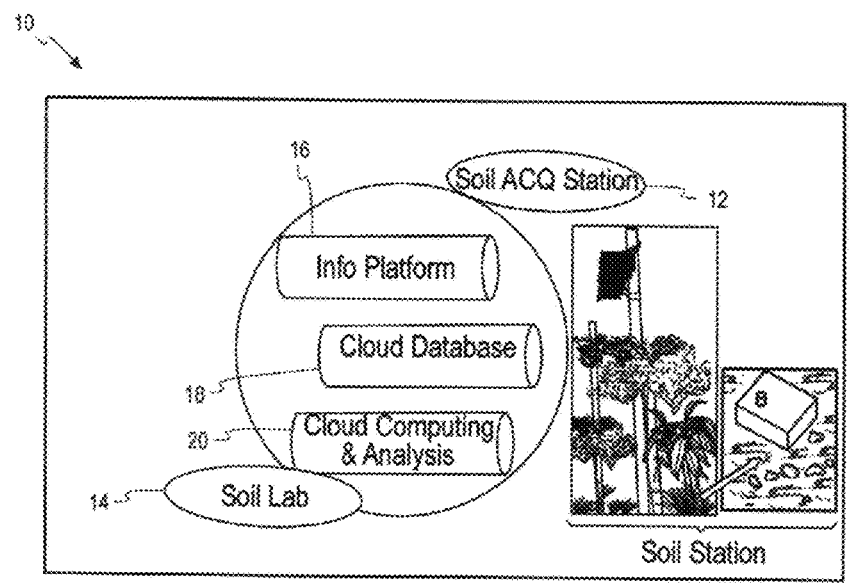
FIG. 1 illustrates a traditional soil sample laboratory exam and fixed soil stationary acquisition methods.

While this invention is susceptible of embodiments in many different forms, there is shown in the drawings and will herein be described in detail a preferred embodiment of the invention with the understanding that the present disclosure is to be considered as an exemplification of the principles of the invention and is not intended to limit the broad aspect of the invention to embodiments illustrated.

Referring first to the system of FIG. 1, a current system 10 is illustrated having a Soil ACQ Station 12, a Soil Lab 14 for analyzing soil samples, and an Information Platform 16 including a Cloud-based database 18 as well as Cloud-based computing and analysis 20. The Station 12 is fixed within a field where it periodically samples soil. The Soil Lab 14 tests each sample and sends the data to be stored in the database 18. From there, the data may be used for further analysis.

With the "Internet of Things" (IoT) and information technologies, the Soil ACQ Station 12 can be positioned remotely while still enabling collection of soil data in real time (e.g., in minutes) and transmission of the collected information and data to the Cloud-based database 18. The Soil Lab 14 can effectively and accurately detect various components of soil. The Soil ACQ Station 12 can upload data on some soil components in real time, but its coverage area affects its accuracy for the entire field, and soil sensors need regular maintenance.

Regarding the accuracy, a singular station does not provide a sufficient sample size for an entire farm field (e.g., hundreds to several thousand acres) where soil data may vary drastically from one fixed area to another only a few hundred feet away. The cost for installation and maintenance of even one fixed station, as well as the obstructive farming issues presented, are obvious. Clearly, the use of several fixed stations for each area of a large field would be even more expensive, more obtrusive to farming, and might still fall short of providing sufficient soil data to improve accuracy. Additionally, using only fixed soil stations requires a large number of human resources and time to map even a small farm field.

Figure 2:
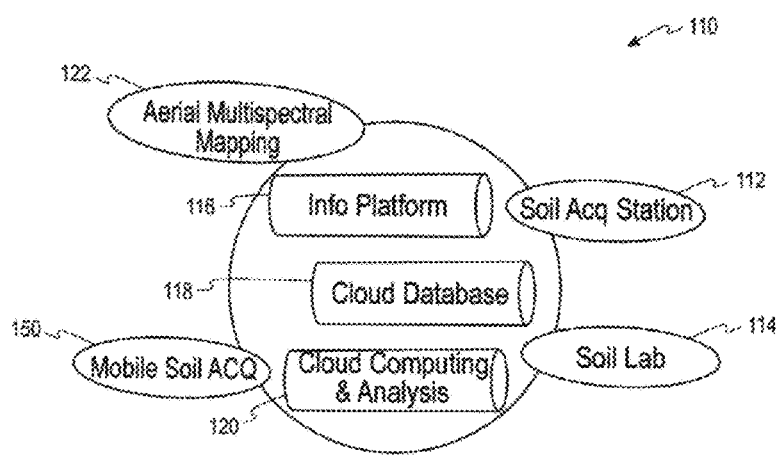
FIG. 2 illustrates an embodiment of the present system with integrated mobile soil sampling capabilities and a multispectral soil scan and mapping system.

Looking now to FIGS. 2-10, there is illustrated an improved system 110, including the implied methods and components of both, for efficiently collecting accurate soil data and using the data to devise effective field management strategies. Generally speaking, as shown in FIG. 2, the system 110 and the related methods of the present invention use an unmanned aerial vehicle (UAV), for aerial-multispectral mapping 132, and a mobile soil acquisition (ACQ) system 150 in combination with the fixed soil acquisition station 112 and an information platform 116 of the prior art system 10.

Figure 3A:
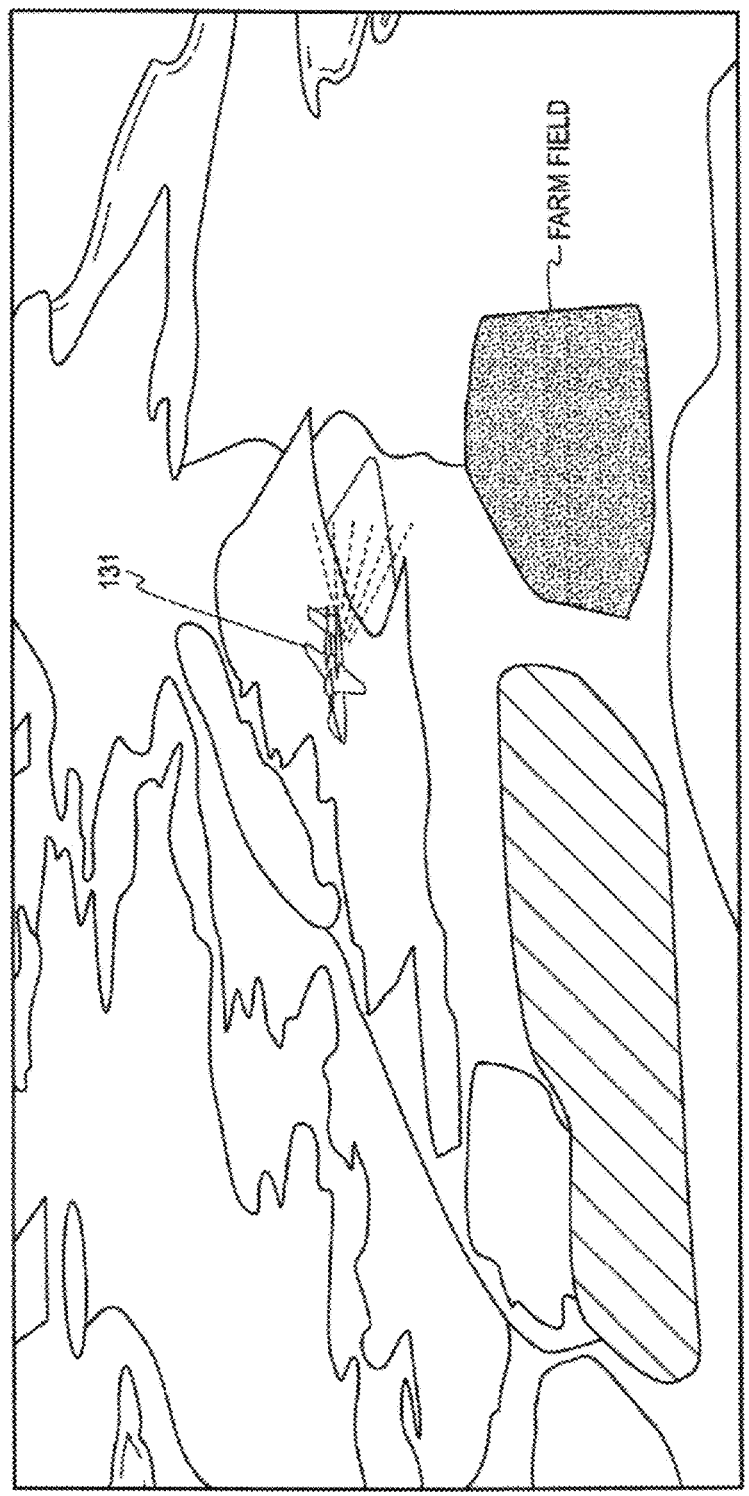
FIG. 3A shows an embodiment of a small Unmanned Aerial Vehicle (UAV) configured with an aerial mapping system which includes Mica-sense Sequoia NIR Camera, light sensor adaptor, RC transmitter, and GPS for scanning and construction of a spectral image.
Figure 3B:
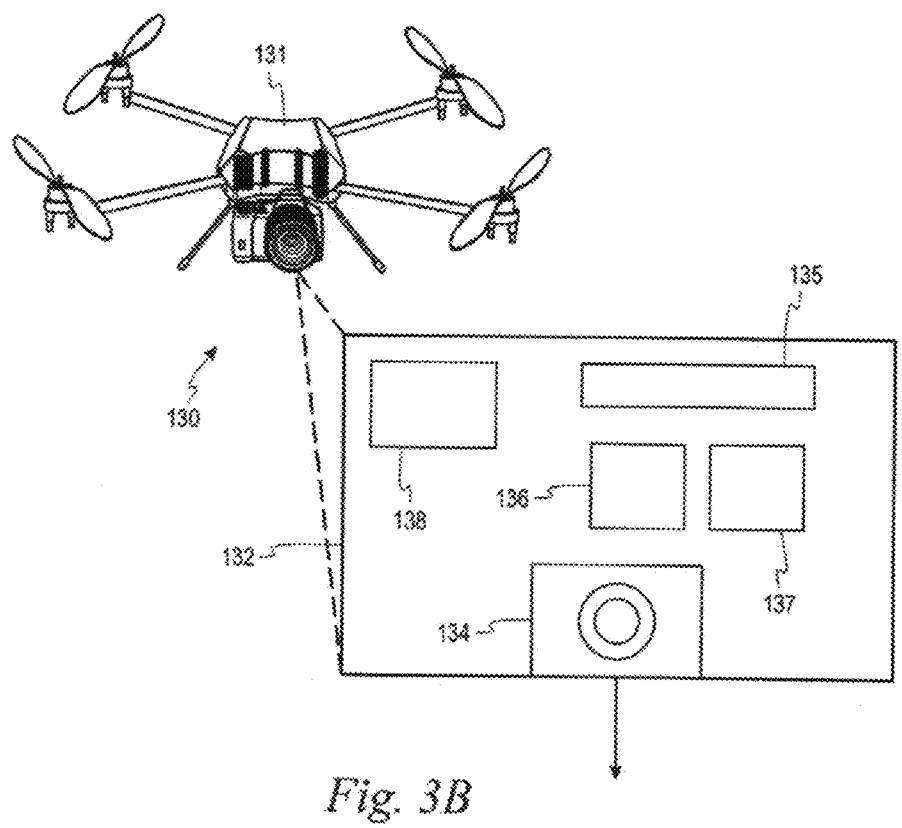
FIG. 3B shows an embodiment of a UAV configured with an aerial mapping system.
Figure 3C:
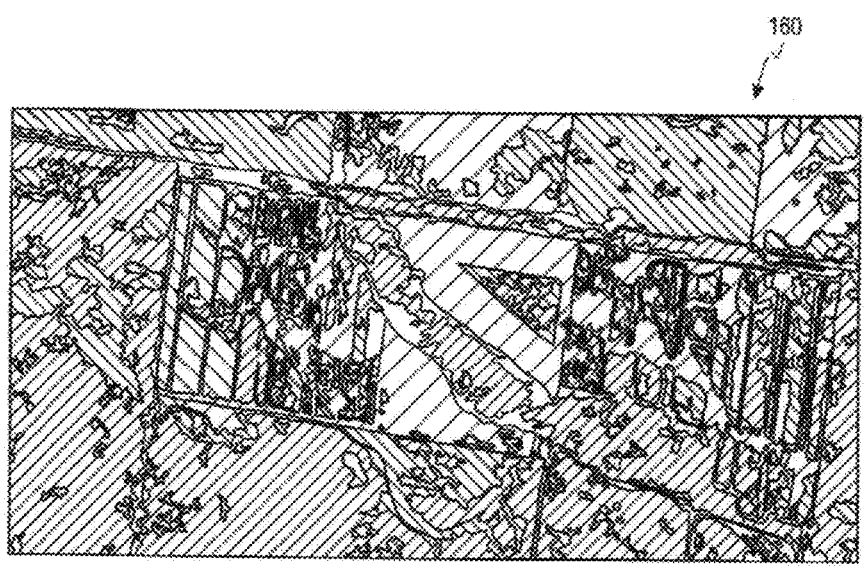
FIG. 3C shows a multispectral image constructed by the UAV aerial mapping system when flying over a farmland.

The UAV 131 of FIGS. 3A-3B is preferably equipped with a penetrating multispectral sensor to scan these large fields from the air. The result of the scan provides a multispectral image 160 of a large area, as shown in FIG. 3C. The field of interest can be extracted from the image as explained below.

The multispectral image 160, such as shown in FIG. 3C, is one that captures image data within specific wavelength ranges across the electromagnetic spectrum. The wavelengths may be separated by filters or by the use of instruments that are sensitive to particular wavelengths, including light sources having frequencies beyond the visible light range, i.e., infrared and ultra-violet. Spectral imaging will allow extraction of additional information the human eye fails to capture with its receptors for red, green and blue. It was originally developed for space-based imaging, but has also found use in document and painting analysis.

An embodiment of a mobile soil sensor system 150 is illustrated in FIG. 4. To acquire the necessary data and map a field, the mobile system 150 is moved through the field to periodically take samples of the soil and analyze each sample for specific soil properties. Regular planned calibrations of the acquired mobile soil data are performed using manual soil sample results from predetermined fixed soil sampling locations on the field. For example, as the mobile system 150 moves through a "transition zone" where sample data changes significantly, a manual soil sample in the "transition zone" may be taken to confirm the accuracy of the data change. If the data from the mobile system 150 is found to be faulty, the fixed soil sample data can be used to calibrate the mobile system data.

The calibration of the mobile system 150 should be distinguished from the calibration of the multispectral image 160 of the UAV system 130. Because the sampling and data acquisition performed by the mobile system 150 typically occurs at a time different from the soil imaging by the UAV 131, it is necessary to account for variances such as time of day, season, weather conditions, and the like. The data from the fixed soil stations 112 can be used to measure the impact of such factors and then synchronize the mobile system 150 data with the UAV image 160 by accounting for the relevant factors.

The positioning of the fixed locations is preferably based on the spectral image (survey) created by the UAV system 130. That is, smaller areas of the desired field are clearly defined by the differing colors of the multispectral image (see FIG. 3C where varying cross-hatching is used to signify different spectral colors). The fixed soil acquisition stations 112 can be strategically positioned to collect samples from each of these defined areas in real time (e.g., in minutes). The collected samples are tested and the results are used to calibrate any variances, such as different acquisition time, between the UAV aerial multispectral mapping image 160 and data from the mobile soil system 150.

As shown in FIG. 9, the calibrated data from the mobile system 150 can be plotted by soil properties, e.g., organic matter (OM), electrical conductivity (EC) and pH. As part of the computing and analysis 120 of the present system 10, a mathematic module is used to calculate a correlation between the spectral image information and the calibrated grid of soil properties, including OM, EC, and soil pH. Eventually, through a growing database of soil data, the correlation of soil properties based on spectral imaging can be greatly improved.

While the present system is generally illustrated in FIG. 2, showing the utilization of both fixed station soil sampling methods and a mobile soil system (Mobile Soil Acq) 150 supplemented with additional components, such as aerial multispectral mapping 122 (see FIGS. 3A-3C), specific preferred components for each system are explained in further detail below.

Mobile Soil Sampling System

In a specific embodiment, a soil sampling system from Veris® Technologies (http://www.veristech.com/) is used to determine soil properties within a subarea of a farm field. Preferably, the mobile system 150 comprises the Mobile Sensor Platform (MSP) 152 which can be attached to a tractor or other vehicle and pulled through a desired field. The MSP 152 is preferably equipped with EC, OM and pH modules, as explained below.

A preferred pH module of the present system is reliable, as it has only one moving part and does not require an operator. A hydraulic cylinder pushes a large soil probe into the ground to allow soil to flow through. When the probe is lifted, soil within is brought into contact with pH electrodes for several seconds. A reading is taken and recorded. The hydraulic cylinder repeats the lowering and lifting motion, forcing the previous sample out of the probe as a new sample flows into the probe, and the electrodes are quickly sprayed and cleaned. The pH module is capable of taking as many as 10 samples per acre.

A preferred EC module is the Veris® Soil EC 3100 (http://www.veristech.com/the-sensors/v3100) which can be attached to the MSP. The EC 3100 has dual-depth electrical arrays for sending and measuring voltage in soil, and data recording capabilities for accurate soil EC information.

A preferred OM module which also couples to the MSP is the Veris® U-Series (http://www.veristech.com/the-sensors/u-series). The module uses a dual-wavelength optical sensor mounted within a specially configured runner shank to allow mapping underneath crop residue and dry surface soil. Subsurface measurement is more accurate as moisture effect is minimized and soil color is primarily related to soil organic matter variations. Readings of soil reflectance are collected in IR and Red wavelengths approximately 60 times a minute through a sapphire window on the bottom of the runner.

For each soil sample taken by the mobile system 150, an OM, EC, and pH value is produced. In the preferred embodiment, the MSP™ system 152 exports the soil data to an output table with OM, pH, and EC values.

TABLES 1-3 below illustrate an example of such data tables for a run of 25 soil samples. With reference to the table headings, TABLE 1 includes "Long" which represents the longitude of the sample; "Lat" represents latitude; "Red" represents the value of the soil reflectivity using an LED source; "IR" represents the value of the soil reflectance of an infrared LED source; "Altitude" represents the position of the sample relative to sea-level; and "Depth" is the distance into the ground where the sample is taken (typically recorded in inches). TABLE 2 includes the headings "OM ratio," which represents the soil organic matter as a percentage (%); "EC SH" and "EC DP" which represent electrical conductivity readings at "shallow" and "deep" points with "EC ratio" being the ratio of EC DP/EC SH; and "CEC" represents a cation exchange capacity for electrical conductivity (in meq/100 g). As to TABLE 3, the heading "pH avg." represents the average pH value of the first two columns, i.e., "pH1" and "pH2". The data can be affirmed and calibrated by fixed sampling data acquired manually based on deviations in the data (e.g., transition zones).

By "calibrated" it is meant that data (i.e., soil sample properties) can be corrected based on the more accurate analysis provided by either manual sampling or by the fixed soil stations. The calibration is used to confirm "transition zones" in mobile sampling as well as to synchronize information between mobile sampling and aerial imagery where other factors, such as weather, season, time of day, etc., differ between the two. These two calibration scenarios are explained in greater detail above. Of course, as the accuracy of the mobile systems improve and as the resulting database grows to account for all factors, the use of a calibration may not be required or may be required less frequently.

TABLE 1

Soil Sample Position Data

| Sample | Long | Lat | Red | IR | Altitude | Depth |
|---|---|---|---|---|---|---|
| 1 | −97.260787 | 38.7413092 | 79.71 | 265.33 | 390.14 | 1.15 |
| 2 | −97.2607861 | 38.741279 | 79.38 | 263.09 | 390.17 | 1.15 |
| 3 | −97.2607858 | 38.7411877 | 79.94 | 265.94 | 390.21 | 1.15 |
| 4 | −97.2607858 | 38.7412177 | 79.83 | 265.03 | 390.2 | 1.15 |
| 5 | −97.2607851 | 38.7412483 | 79.43 | 263.59 | 390.19 | 1.15 |
| 6 | −97.2607849 | 38.7411582 | 79.78 | 267.01 | 390.22 | 1.15 |
| 7 | −97.2607843 | 38.7413709 | 80.51 | 269.9 | 390 | 1.15 |
| 8 | −97.2607838 | 38.7411294 | 79.54 | 267.15 | 390.23 | 1.16 |
| 9 | −97.2607837 | 38.7414016 | 81.04 | 269.1 | 389.92 | 1.17 |
| 10 | −97.2607835 | 38.7410994 | 78.98 | 264.8 | 390.26 | 1.17 |
| 11 | −97.260783 | 38.7414315 | 81.6 | 268.1 | 389.86 | 1.17 |
| 12 | −97.2607826 | 38.7410684 | 78.94 | 264.21 | 390.3 | 1.17 |
| 13 | −97.260782 | 38.7414609 | 82.17 | 270.39 | 389.83 | 1.16 |
| 14 | −97.2607818 | 38.7414905 | 81.97 | 271.67 | 389.82 | 1.16 |
| 15 | −97.2607812 | 38.7415207 | 81.09 | 270.16 | 389.81 | 1.18 |
| 16 | −97.2607811 | 38.7428827 | 81.34 | 278.74 | 388.23 | 1.15 |
| 17 | −97.260781 | 38.7408272 | 80.32 | 269.59 | 390.72 | 1.16 |
| 18 | −97.260781 | 38.7408574 | 78.99 | 264.48 | 390.65 | 1.16 |
| 19 | −97.2607808 | 38.7430354 | 82.48 | 286.85 | 388.44 | 1.17 |
| 20 | −97.2607808 | 38.7429133 | 81.27 | 279.14 | 388.27 | 1.14 |
| 21 | −97.2607807 | 38.7403208 | 84.24 | 275.26 | 391.79 | 1.15 |
| 22 | −97.2607804 | 38.7446256 | 87.93 | 300.17 | 390.89 | 1.12 |
| 23 | −97.2607804 | 38.7429749 | 82.21 | 285.1 | 388.33 | 1.13 |
| 24 | −97.2607804 | 38.7408874 | 77.51 | 260.44 | 390.57 | 1.16 |
| 25 | −97.2607803 | 38.7402949 | 84.73 | 277.28 | 391.84 | 1.17 |

TABLE 2

OM and EC Soil Data

| Sample | OM ratio | EC SH | EC DP | EC Ratio | CEC |
|---|---|---|---|---|---|
| 1 | 3.33 | 43.81 | 57.41 | 1.31 | 24.34 |
| 2 | 3.31 | 44.79 | 60.24 | 1.34 | 24.56 |
| 3 | 3.33 | 42.38 | 59.76 | 1.41 | 24.01 |
| 4 | 3.32 | 43.63 | 61.27 | 1.4 | 24.3 |
| 5 | 3.32 | 44.59 | 61.65 | 1.38 | 24.51 |
| 6 | 3.35 | 41.1 | 58.14 | 1.41 | 23.72 |
| 7 | 3.35 | 40.28 | 51.66 | 1.28 | 23.53 |
| 8 | 3.36 | 40.33 | 56.91 | 1.41 | 23.55 |
| 9 | 3.32 | 40.79 | 52.86 | 1.3 | 23.65 |
| 10 | 3.35 | 40.16 | 56.5 | 1.41 | 23.51 |
| 11 | 3.29 | 42.17 | 55.22 | 1.31 | 23.96 |
| 12 | 3.35 | 40.54 | 57.08 | 1.41 | 23.59 |
| 13 | 3.29 | 43.71 | 57.13 | 1.31 | 24.31 |
| 14 | 3.31 | 44.76 | 58.07 | 1.3 | 24.55 |
| 15 | 3.33 | 45.46 | 58.28 | 1.28 | 24.71 |
| 16 | 3.43 | 54.67 | 67.76 | 1.24 | 26.81 |
| 17 | 3.36 | 45.52 | 63.59 | 1.4 | 24.73 |
| 18 | 3.35 | 44.54 | 60.1 | 1.35 | 24.5 |
| 19 | 3.48 | 47.99 | 64.93 | 1.35 | 25.29 |
| 20 | 3.43 | 52.98 | 67.17 | 1.27 | 26.42 |
| 21 | 3.27 | 42.56 | 47.04 | 1.11 | 24.05 |
| 22 | 3.41 | 51.92 | 57.84 | 1.11 | 26.18 |
| 23 | 3.47 | 51.24 | 66.91 | 1.31 | 26.03 |
| 24 | 3.36 | 42.62 | 55.74 | 1.31 | 24.07 |
| 25 | 3.27 | 40.7 | 43.03 | 1.06 | 23.63 |

TABLE 3 pH Soil Data

| Sample | pH1 | pH2 | pH Avg. |
|---|---|---|---|
| 1 | 6.23 | 6.01 | 6.12 |
| 2 | 6.36 | 5.97 | 6.17 |
| 3 | 6.38 | 6.23 | 6.31 |
| 4 | 6.23 | 6.20 | 6.21 |
| 5 | 6.40 | 6.05 | 6.22 |
| 6 | 6.32 | 6.03 | 6.18 |
| 7 | 6.32 | 6.10 | 6.21 |
| 8 | 6.40 | 6.03 | 6.21 |
| 9 | 6.16 | 6.16 | 6.16 |
| 10 | 6.10 | 6.10 | 6.10 |
| 11 | 6.71 | 6.44 | 6.57 |
| 12 | 6.57 | 5.84 | 6.20 |
| 13 | 6.01 | 5.92 | 5.96 |
| 14 | 6.47 | 6.14 | 6.31 |
| 15 | 6.73 | 6.73 | 6.73 |
| 16 | 6.95 | 6.99 | 6.97 |
| 17 | 7.18 | 7.12 | 7.15 |
| 18 | 7.49 | 7.31 | 7.40 |
| 19 | 7.18 | 7.14 | 7.16 |
| 20 | 6.97 | 6.60 | 6.79 |
| 21 | 6.97 | 6.53 | 6.75 |
| 22 | 6.97 | 6.31 | 6.64 |
| 23 | 6.49 | 6.42 | 6.45 |
| 24 | 6.42 | 6.12 | 6.27 |
| 25 | 6.40 | 6.03 | 6.21 |

Using the data and GPS coordinates, the samples can be reconstructed as three 2-D grids or lattices 154. That is, one of each lattice includes data for OM, EC, and pH values, as illustrated in FIG. 9. With the use of on-board GPS 156, the resulting soil sample grids 154 can be aligned to a spectral image 160 (see FIG. 7) constructed by the UAV system 130.

Aerial Mapping Vehicle

As illustrated in FIGS. 3A and 3B, the UAV 131 is comprised of a drone which flies above a field in a predetermined pattern to scan the farmland and construct a spectral image 160 (FIG. 3C). The resulting image 160 is able to register those fields covered by the image using the GPS information. The parameters of these fields are able to be outlined on the spectral image (e.g., FIG. 5). The drone of the UAV 131 can be any suitable device capable of operating while being equipped with an aerial mapping system 132, including a camera 134, light sensor adaptor 135, RC transmitter 136, GPS 137, and image processing software 138. Using this equipment, the UAV system 130 can be customized for soil mapping as described below with reference to FIG. 3.

FIG. 3B shows a small Unmanned Aerial Vehicle (UAV) 131 configured with an aerial mapping system 132 which preferably includes a Micasense Sequoia™ NIR (or equivalent) camera 134 (see https://www.micasense.com/parrotsequoia/), as well as the light sensor adaptor 135, RC transmitter 136, and a GPS 137. In some cases, the camera is equipped with at least some of these features.

Due to a limited field of view of the multispectral camera, the UAV system 130 may need to take many pictures when flying over a field. These pictures will overlap one another and, with the further benefit of the GPS information for each picture, a final spectral image can be constructed from the plurality of overlapping pictures taken from the air by the UAV 131. A final spectral image 160 can be segmented into several obvious zones according to image pixel density using a process called thresholding. Each zone addresses relative consistent soil properties such as OM, EC, and pH values. The image 160 can then be used to determine positioning of fixed soil sample stations 112 for the soil laboratory exam. For example, a fixed station 112 may be positioned according to zone information, such as pixel density and their location. The results of the fixed soil sample stations 112 are used to calibrate the mobile soil sensor system data.

System Computing and Analysis

Figure 5:
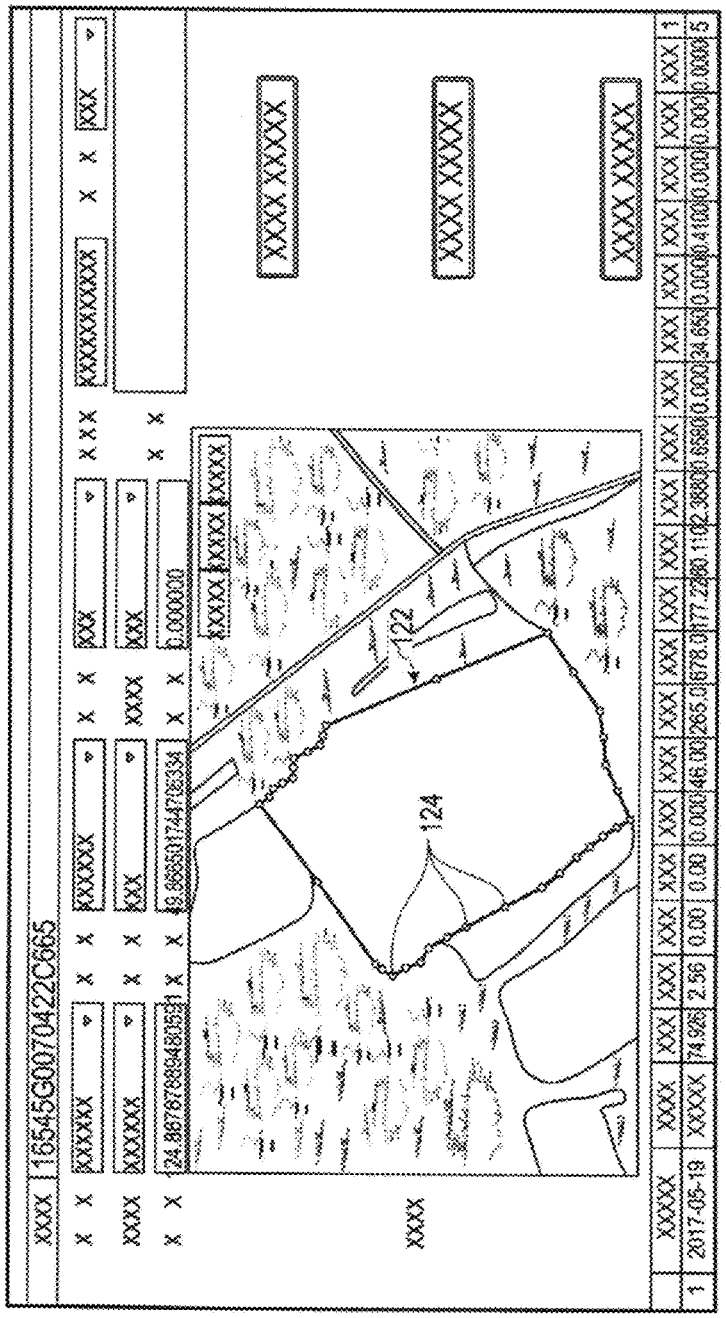
FIG. 5 shows a particular field located by GOOGLE® Maps using GPS acquired coordinates (i.e., longitude and latitude) and using pylon vertices to outline the particular field.

In addition to its soil properties, a farmland shown in FIG. 5 usually has a serial number, administrative address (more than one entry), owner name, and GPS (i.e., longitude, latitude and altitude) information. With the GPS information, the area can be located on a mapping program, for example, Google® Maps (https://www.google.com/maps/). Following the landscape of the field, using a polygon drawing tool, an outline 124 of the field is able to be created with a plurality of vertices 126 (see FIG. 5). Using these vertices 126 associated with the GPS information, a region of interest (ROI) 128 can be extracted from the spectral image 160 (FIG. 3C) which is then aligned to the field.

Figure 6:
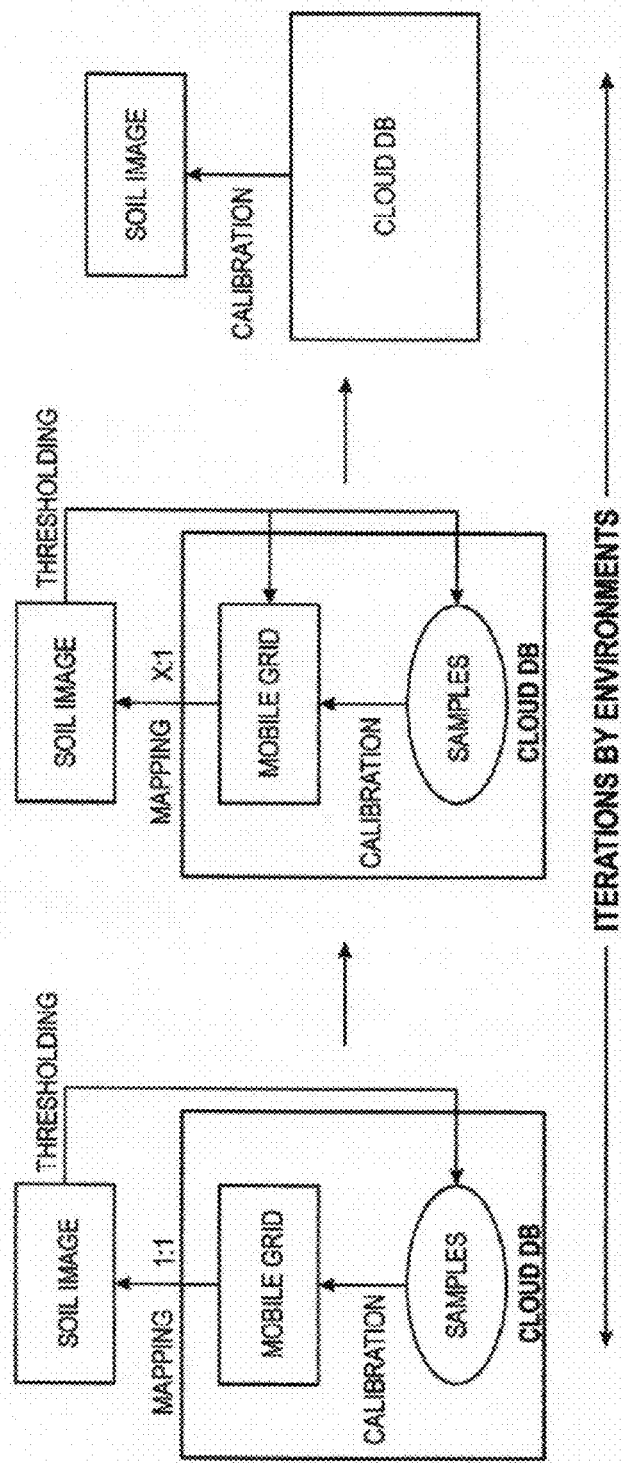
FIG. 6 is a chart showing an embodiment of an iterative method combining multispectral soil mapping, mobile ongoing soil sample grid, and traditional soil sampling to learn corresponding relationships and create a large database.

FIG. 6 shows three stages of a preferred process for creating a useful soil property database. In an early stage (1), a spectral image 160 (FIG. 5) from a UAV 131 is able to be segmented into several regions using a well-known thresholding technique. These regions can be used to determine the locations of fixed-point soil stations 112 for sampling (i.e., using traditional soil lab exam). The results of the fixed-point sampling are used to calibrate the deviation of the results of the onboard mobile sensor system data to create a lattice of data points on soil properties. Using GPS positioning, the lattice or grids 154 can be projected onto the spectral image (see FIG. 8) and the pixel resolution of the spectral image can be extrapolated through a bilinear or bi-cubic sampling method (interpolation).

In a middle stage (2) of FIG. 6, the mapping area of the aerial image is increased (preferably in the range of 10-100 times larger) using the same method. That is, manual spot sampling areas are determined for mobile sensor system to acquire data and for fixed-points soil labs to calibrate. Repeating this method gradually expands the coverage of UAV aerial image, according to specific soil structure, region, environment, season, climate, etc.

Finally in a later stage (3), after sufficient iterations of the sampling and correlation, a real-time spectral image calibration can be achieved and can be used for the determination of OM, EC, and pH values.

Although the resulting soil sample grids 154 have a different resolution than that of the spectral image 160, each pixel's geometric location represents OM, EC, or pH data using bilinear interpolation or bicubic interpolation weighted by the pixel density of soil samples. The pixel density of the spectral image varies based on the type of soil (location), four seasons (weather attributes), and agriculture processes (including fertilizing and planting). There is a definite correlation between varying spectral images of the same field. One way to realize and fine-tune this correlation is to acquire greater data points and by using mathematical modeling (Cloud Database and Computing).

In the final stage (3) of the process, using the Cloud-based database and computing, historic data of soil can be referenced to distinguish the type of soil and determine where and how big sub-region sample grids must be. Using the correlation of the spectral image variations and soil properties, e.g., OM, EC, and pH values, spectral mapped area not covered by the mobile sampling grids 154 (see, for example, FIG. 8) can be mapped with the information of nearby sample grids and the mathematics. Repeated data collections, including during different seasons, various weather conditions, and diverse agriculture practices, further improves the weighted bilinear or bi-cubic interpolation relied on at stage (3) of FIG. 6.

Figure 7:
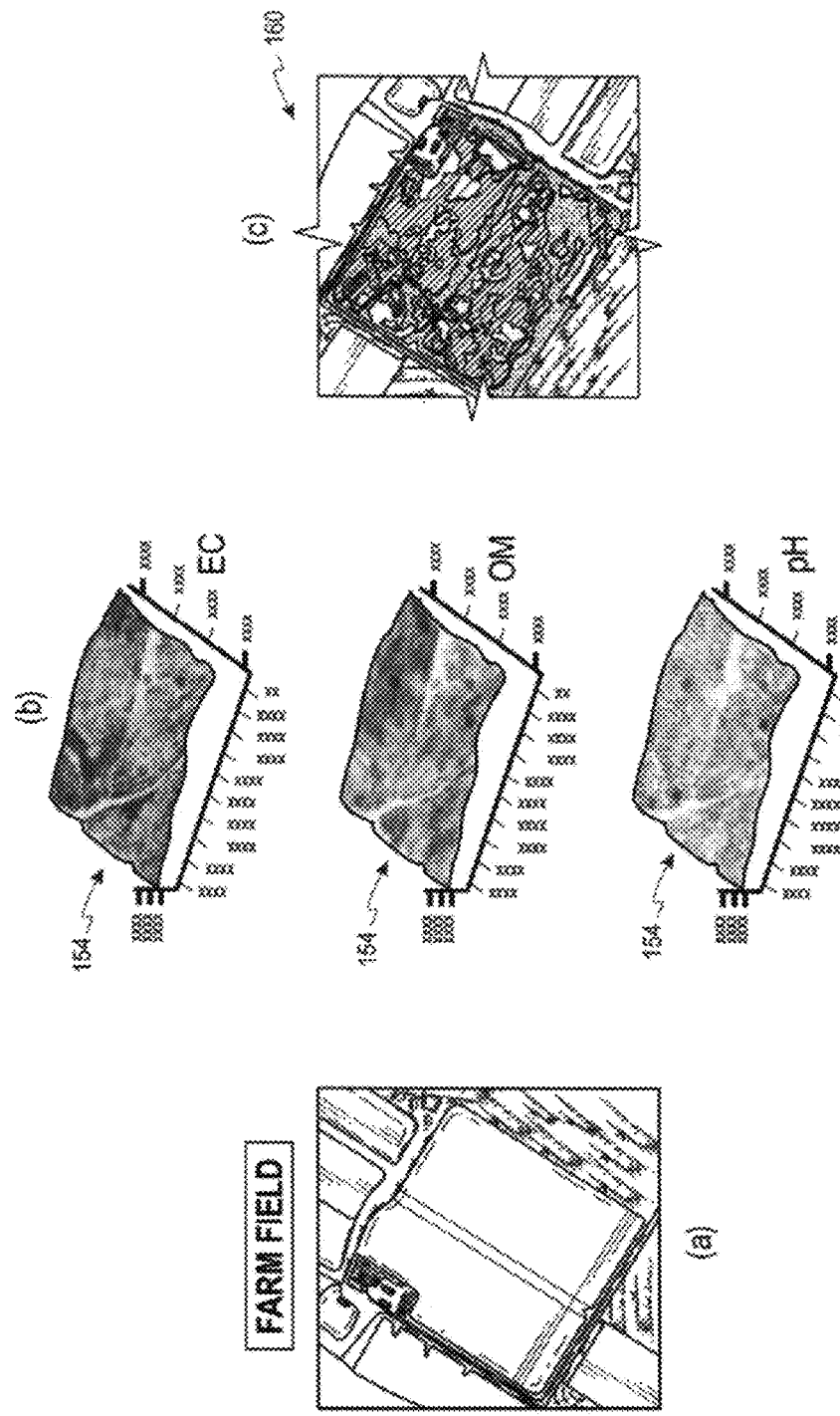
FIG. 7 is a group of three illustrations of a farm field showing the field as (a) an aerial view, (b) mapped by soil properties, and (c) a multispectral image.
Figure 8:
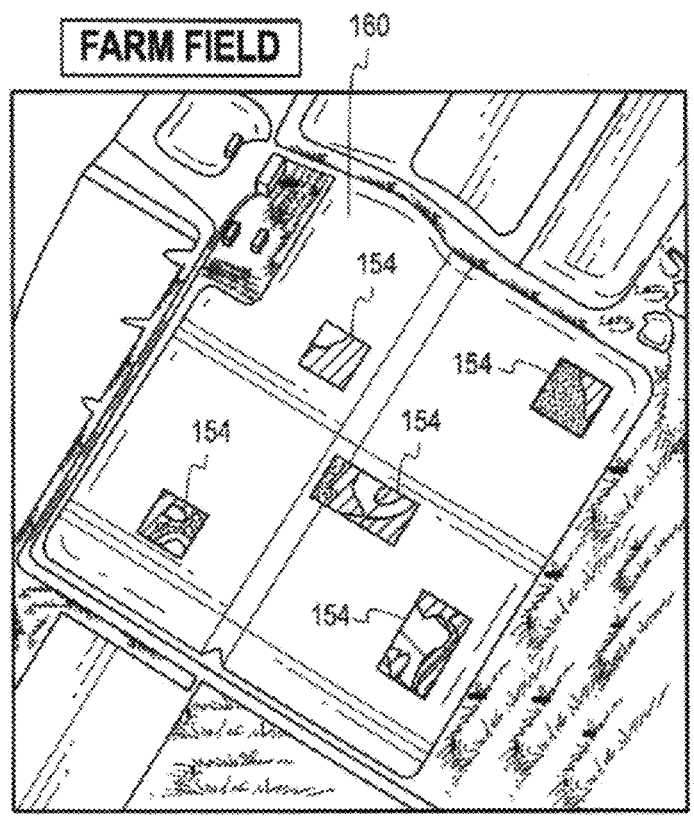
FIG. 8 is an aerial image of a field with several overlaid multispectral areas.

With reference to FIG. 7, a correspondence between the spectral image 160 produced by the UAV 131 and the construction of the lattice 154 (e.g., OM, EC, and pH data), can be made by aligning the images using GPS coordinates. As previously noted, the whole spectral image can be divided into several regions (e.g., aerial multispectral mapping) by image thresholding. These regions are based on fixed-points soil lab samples.

To expand the coverage of the spectral image, according to the segmentation of image threshold, the data acquisition areas of mobile system 150 and the related fixed-point soil lab samples are determined. Five segments are illustrated in the spectral image of FIG. 8. The soil data platforms provide information such as soil type (e.g., brown coniferous forest soil, black soil, chernozemic, etc.), cultivated land type (e.g., irrigated, dry-land, paddy field, etc.), and soil agrochemical analysis data as a reference for data models, providing corrective biases for mobile system 150 data grids 154 and the spectral image 160 of the UAV 131. As noted, the more correlative data acquired, the greater the determinative accuracy of the spectral image becomes.

By further enlargement of the scanned area or by exploring totally different areas and soil types, with the iterative process described above, eventually a mathematic model with a significant database in the Cloud can be developed such that a spectral image acquired by UAV can be directly interpolated to soil properties for OM, EC, and pH values.

The present invention also depends on software applications running, preferably in the Cloud. The software is used to: 1) accept data transmitted from (a) sensors, such as pH sensors installed on the fixed soil sample station, (b) soil labs after manual input of laboratory results (e.g., through conducting manual soil samples), and (c) mobile soil sensor systems (MSP and UAV as data grids and images); 2) transform data to a common format, such as JSON Package, a JavaScript Object Notation light weight data exchange format; 3) transfer the transformed data to a Cloud-based database and computing server for analysis (calibration); and 4) push to web applications running in the Cloud for services.

As part of the information platform, a Cloud-based database is used for collecting and storing data from the fixed station and mobile system and for collecting the plurality of images produced by the UAV mapping system. The computing system of the platform is electronically coupled to the database and is configured to use the data from the lab to calibrate data from the mobile system and then use the calibrated data to produce at least one grid representing the second land area with soil property values.

The computing system also comprises a correlation system (e.g., software) and interpolation system (e.g., software). The correlation system aligns the at least one grid onto a corresponding portion of the multispectral image and correlates the calibrated data to discernible regions of the portion to create mapped regions. The interpolation system assigns soil property values to the remainder of the field (i.e., that portion which has not been mapped by the mobile system) based on discernible regions of the multispectral image similar to the mapped regions.

Figure 10:
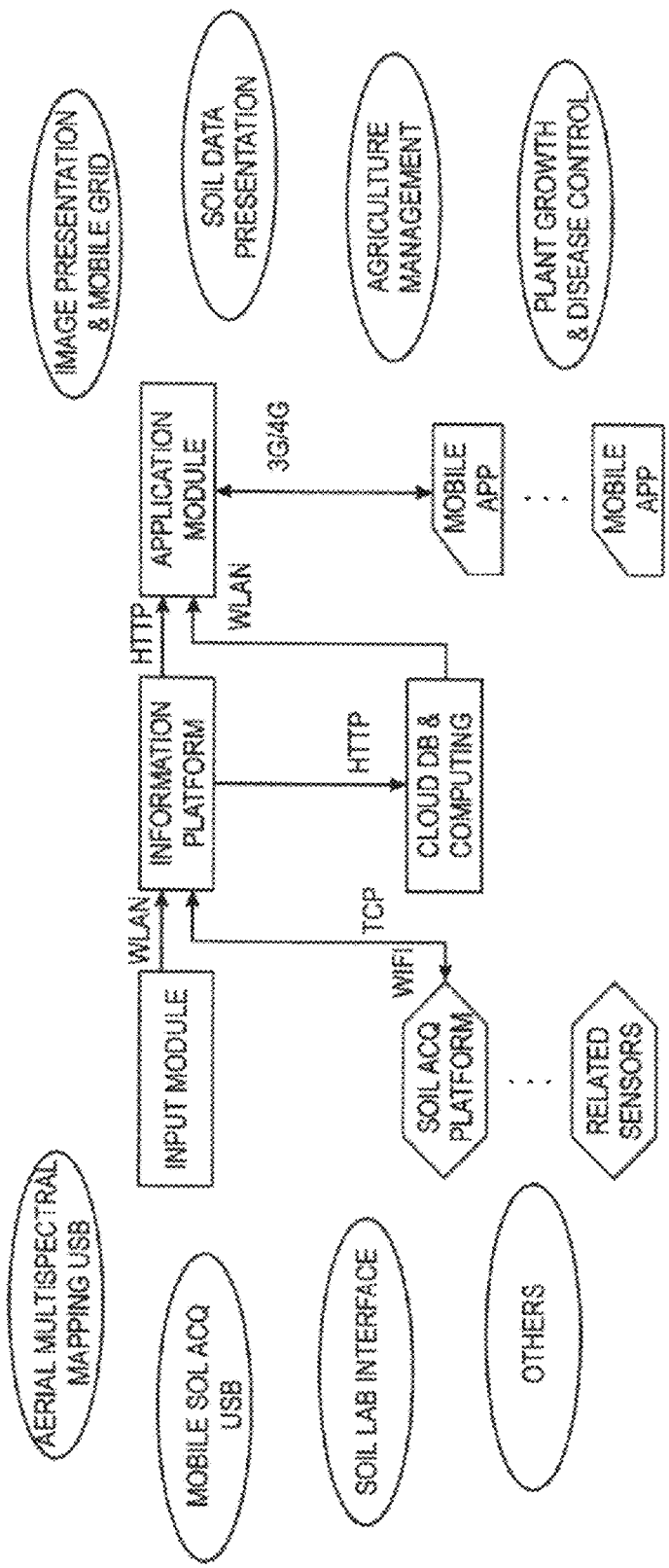
FIG. 10 is a block diagram of an embodiment of a cloud-based database and application platform for soil data.

FIG. 10 is the system framework of a Cloud-based soil exam platform for farmland. The information platform and data analysis component (including storage) are core components of the system framework. These components provide various types of soil sensors and laboratory data input modules, and together they are capable of translating, connecting, pushing, analyzing, accumulating, and storing data. Over time, the spectral image of UAV can be real-time calibrated and the information of OM, EC, and pH can be effectively addressed and viewed as an image.

Example Method

In an exemplary method, a 1000 acre farm field is desired to be mapped for EC, OM and pH soil properties to derive a soil management strategy. Using the system of the present disclosure, a UAV 131 is flown over the field to obtain a multispectral image 160 of the entire 1000 acres. The image may be pieced together from a plurality of overlapping photos taken. A mobile soil system 150 is moved systematically across a predetermined portion of the entire field, e.g., a 10 acre area. The mobile system 150 acquires initial soil property data for a plurality of soil samples. A grid of the initial soil property data is constructed and correlated to a corresponding area of the multispectral image. That is, the 10 acre area is overlaid onto a corresponding area of the multispectral image. This may be repeated for additional 10 acre areas until a desired portion of the 1000 acre farm field is overlaid with soil property grids. Using the correlated grid(s) and initial soil property data, soil property data for the remainder of the entire field (i.e., that portion not covered by a grid) can be extrapolated based on the multispectral image of the remainder of the field. For example, similar multispectral hues can be assumed to have similar soil properties.

The number of smaller grids constructed and overlaid to the multispectral image will increase the accuracy of extrapolation. Of course, all the extrapolation is done using computer software which can look at each pixel of the multispectral image to achieve greater accuracy.

Of course, it takes a fraction of the time to create the multispectral image than it does to create each grid, so there may be a notable disjunction between the time of the initial soil data to the time of the multispectral image. This time span may introduce factors, such as a change in weather, season, time of day, etc., which may alter soil properties. To account for the time lapse between events, the initial soil property data may need to be synchronized with the multispectral image. This is accomplished using fixed soil sampling stations positioned within the field.

The synchronizing is accomplished by positioning at least one fixed soil sampling station in an area on the field. The station can then take additional soil samples during the span of time, as frequently as necessary. The samples are tested to acquire additional soil property data. This data indicates the effect of these time factors on soil in the field. Accordingly, correction factor for soil data can be acquired from the additional soil property data to account for the span of time. The determined correction factor is then applied to the initial soil property data to account for the appropriate time difference.

Additionally, the method and system may also require calibration of the initial soil property data of the mobile soil system. Occasionally, the initial soil property data may seem questionable due to a significant change from one area of the field to another. Calibration requires only that a manual confirmation soil sample(s) be taken at strategic points in the predetermined portion of the field. The strategic points should coincide with any area with questionable soil property data. These samples are tested to acquire confirming soil property data, which is then checked against the initial soil property data for the same strategic points in the predetermined portion of the field. If the initial data is off, it can be corrected using the confirming soil property data.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicants' contribution. The actual scope of the protection sought is intended to be defined in the following claims when viewed in their proper perspective based on the prior art.

What is claimed is:

1. A system for mapping soil properties of a field, the system comprising:
   a multispectral image mapping system configured to produce a multispectral image for a first land area having a defined periphery, the multispectral image having a plurality of discernible regions;
   a mobile soil sensor system comprising a connector for attachment to a vehicle to allow moving the sensor system over a second land area, a soil sampling mechanism which takes periodic samples of soil as the system moves over the second land area, a GPS module for determining a location for each soil sample, at least a first soil sensor for determining a desired property of each soil sample, and memory for recording soil sample properties and location as soil data, wherein the second land area is completely within the periphery of the first land area;
   a database for collecting and storing the soil data from the mobile system and for collecting images produced by the mapping system;
   a computing system electronically coupled to the database and configured to use the soil data from the mobile system to produce at least one grid representing the second land area with soil property values, the computing system comprising:
      a correlation system for aligning the at least one grid onto a corresponding portion of the multispectral image and correlating soil data to discernible regions of the corresponding portion to create mapped regions; and
      an interpolation system for assigning soil properties to remaining portions of the first land area which are not part of the second land area, wherein the assigned soil properties are based on the mapped regions.

2. The system of claim 1, further comprising an unmanned aerial vehicle (UAV) for flying above an area to be mapped, wherein the spectral image mapping system is mounted to the unmanned aerial vehicle (UAV).

3. The system of claim 2, wherein the UAV comprises a drone.

4. The system of claim 2, wherein the spectral image mapping system further comprises a multispectral imaging camera attached to the UAV.

5. The system of claim 1, wherein the soil property determined is selected from the group consisting of organic matter (OM), electrical conductivity (EC) and pH.

6. The system of claim 1, further comprising at least one fixed soil sampling station positioned at a known location within the first land area and configured to take periodic samples of soil proximate the fixed station position.

7. The system of claim 6, further comprising a soil lab for analyzing the samples from the fixed station, determining a soil property for each sample, and recording the soil property as calibration data, wherein the calibration data is used to calibrate the soil sample data to produce accurate soil data.

8. The system of claim 7, wherein the accurate soil data is used by the computing system to produce at least one grid representing the second land area with soil property values.

9. The system of claim 6, further comprising a plurality of fixed soil sampling stations wherein at least one fixed soil sampling station is positioned in the field corresponding to each discernible region of the multispectral image.

10. A method of mapping soil properties of a field, the method comprising the steps of:
    obtaining a multispectral image of an entire field, such as a farm field;
    acquiring initial soil property data for a plurality of soil samples by moving a mobile soil sensor system over a predetermined portion of the entire field, wherein the predetermined portion is smaller than the entire field;
    constructing a grid of the initial soil property data;
    correlating the grid and its soil property data to a corresponding area of the multispectral image; and
    using the correlated grid and initial soil property data to extrapolate an estimated soil property to a remainder of the field, the remainder of the field being a portion not covered by the predetermined portion, based on the multispectral image of the remainder of the field.

11. The method of claim 10, further comprising the step of repeating the steps of acquiring, constructing and correlating for a second area of the field before the step of using the correlated grid and initial soil property data to extrapolate.

12. The method of claim 10, wherein the step of obtaining a multispectral image comprises the steps of:
    flying an unmanned aerial vehicle equipped with a multispectral imaging camera over the entire field;
    taking a plurality of pictures of the field; and
    constructing the multispectral image from the plurality of pictures.

13. The method of claim 10, wherein the soil properties include organic matter (OM), electrical conductivity (EC) and pH.

14. The method of claim 10, wherein the step of obtaining a multispectral image and acquiring initial soil property data occur at different times during a span of time.

15. The method of claim 14, further comprising the step of synchronizing the initial soil property data with the multispectral image to account for the different times.

16. The method of claim 15, wherein the step of synchronizing comprises the steps of:
    positioning a fixed soil sampling station in an area on the field;
    taking additional soil samples from the fixed station frequently during the span of time;
    testing the additional soil samples to acquire additional soil property data;
    determining a correction factor for soil data acquired during the span of time; and
    applying the correction factor to the initial soil property data to account for the time difference.

17. The method of claim 10, further comprising the step of calibrating the initial soil property data of the plurality of soil samples.

18. The method of claim 17, wherein the step of calibrating the initial soil property data comprises the steps of:
    manually taking confirmation soil samples at strategic points in the predetermined portion of the field;
    testing the confirmation soil samples to acquire confirming soil property data; and checking the confirming soil property data against the initial soil property data for the strategic points in the predetermined portion of the field; and correcting the initial soil property data if significantly different from the confirming soil property data.

* * * * *